(12) United States Patent
Marhold et al.

(10) Patent No.: US 6,441,239 B1
(45) Date of Patent: Aug. 27, 2002

(54) PROCESS FOR PREPARING 2-(4-TRIFLUOROMETHOXYPHENYL) ETHYLAMINE AND 4-BROMOMETHYL- AND 4-CHLOROMETHYL-1-TRIFLUOROMETHOXYBENZENE

(75) Inventors: Albrecht Marhold, Leverkusen; Peter Müller, Odenthal, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/029,535

(22) Filed: Dec. 20, 2001

(30) Foreign Application Priority Data

Dec. 27, 2000 (DE) .......................................... 100 65 442

(51) Int. Cl.[7] .......................................... C07C 209/00
(52) U.S. Cl. .................................. 564/375; 564/374
(58) Field of Search ................................ 564/374, 375

(56) References Cited

U.S. PATENT DOCUMENTS 6,232,475 B1   5/2001   Müller et al. ............... 549/362

*Primary Examiner*—Samuel Barts
(74) *Attorney, Agent, or Firm*—Joseph C. Gil; Richard E. L. Henderson

(57) ABSTRACT

The invention relates to a process for preparing 2-(4-trifluoromethoxyphenyl)ethylamine in an advantageous manner by
(a) converting trifluoromethoxybenzene by halomethylation into halogenomethyl-1-trifluoromethoxybenzene,
(b) converting the halogenomethyl-1-trifluoromethoxybenzene by halogen-cyano exchange into 4-(trifluoromethoxyphenyl)acetonitrile, and
(c) reducing the 4-(trifluoromethoxyphenyl)acetonitrile using hydrogen in the presence of a nickel catalyst to form 2-(4-trifluoromethoxyphenyl)ethylamine.

The first step of this process also represents an advantageous process for preparing 4-bromomethyl- and 4-chloromethyl-1-trifluoromethoxybenzene.

7 Claims, No Drawings

PROCESS FOR PREPARING 2-(4-TRIFLUOROMETHOXYPHENYL) ETHYLAMINE AND 4-BROMOMETHYL- AND 4-CHLOROMETHYL-1-TRIFLUOROMETHOXYBENZENE

BACKGROUND OF THE INVENTION

The present invention relates to an improved process for preparing 2-(4-trifluoromethoxyphenyl)ethylamine and 4-bromomethyl- and 4-chloromethyl-1-trifluoromethoxybenzene from trifluoromethoxybenzene.

2-(4-Trifluoromethoxyphenyl)ethylamine is an important inter-mediate for preparing agrochemically active compounds.

It is already known that 2-(4-trifluoromethoxyphenyl) ethylamine can be prepared by reacting 1-bromo-4-(trifluoromethoxy)benzene with N-vinyl-succinimide in a Pd-catalyzed Heck reaction and then subjecting the reaction product to a hydrogenation and finally subjecting the hydrogenation product to a hydrazinolysis (see DE-A 1 98 59 684 and DE-A 1 99 81 223). This process is not particularly suitable for implementation on an industrial scale since Pd catalysts, which are very expensive, are required for the Heck reaction and the subsequent hydrogenation. Moreover, a succinyl radical, which must be cleaved off in order to obtain the desired product, is carried through the synthesis. Its handling is associated with great expense, as well as with a view to its disposal or recycling into N-vinyl-succinimide that can be reused.

Accordingly, there is still a need for an efficient process for preparing 2-(4-trifluoromethoxyphenyl)ethylamine that can also be carried out favorably on an industrial scale.

It is also known that 4-bromomethyl- and 4-chloromethyl-1-trifluoromethoxybenzene can be prepared in a four-step process, starting from 4-methoxybenzoyl chloride. Here, 4-methoxybenzoyl chloride is initially chlorinated to give 4-(trichloromethoxy)benzoyl chloride that is converted by treatment with hydrofluoric acid into 4-(trifluoromethoxy) benzoyl fluoride. This benzoyl fluoride is then reduced with lithium aluminum hydride to give 4-(trifluoromethoxy) benzyl alcohol that is finally converted with hydrobromic acid into 4-bromomethyl-1-trifluoromethoxybenzene or by treatment with thionyl chloride into 4-chloromethyl-1-trifluoromethoxy benzene. Due to the fact that it involves four steps and that the handling of lithium aluminum hydride is required, this process is very complicated, making it, too, relatively unsuitable for an industrial application. Accordingly, a person skilled in the art will not consider using 4-bromomethyl- and 4-chloromethyl-1-trifluoromethoxybenzene as intermediates for an efficient preparation of 2-(4-trifluoromethoxyphenyl)ethylamine. Hitherto, 4-bromomethyl- and 4-chloromethyl-1-trifluoromethoxybenzene have been used for preparing only small amounts of special active compounds of no commercial importance.

SUMMARY OF THE INVENTION

We have now found a process for preparing 2-(4-trifluoromethoxyphenyl)ethylamine comprising (a) converting trifluoromethoxybenzene by halomethylation into 4-halogenomethyl-1-trifluoromethoxybenzene, (b) converting the 4-halogenomethyl-1-trifluoromethoxybenzene by halogen-cyano exchange into (4-trifluoromethoxyphenyl)acetonitrile, and (c) reducing the (4-trifluoromethoxyphenyl)acetonitrile using hydrogen in the presence of a nickel catalyst to form 2-(4-trifluoromethoxyphenyl)ethylamine.

DETAILED DESCRIPTION OF THE INVENTION

Trifluoromethoxybenzene, the starting material required for the first step, is an industrial product and commercially available.

Conversion of the trifluoromethoxybenzene into a 4-halogenomethyl-1-trifluoromethoxybenzene can be carried out using, for example, formaldehyde and hydrogen bromide, if appropriate in the presence of a Lewis acid and/or a protic acid as catalyst. The hydrogen bromide can also be generated in situ from a bromide (for example, an alkali metal bromide), and a strong acid. It is also possible to use sodium bromide in the presence of a Lewis acid and/or a protic acid as catalyst. Suitable Lewis acids are, for example, zinc chloride and aluminum chloride, and suitable protic acids are, for example, phosphoric acid and sulfuric acid. The amount of Lewis acid or protic acid catalysts can be, for example, from 0.1 to 100 mol % (preferably from 5 to 10 mol %), based on the trifluoromethoxybenzene used. The formaldehyde is preferably employed in the form of paraformaldehyde. Per mole of trifluoromethoxybenzene, it is possible to use, for example, from 1 to 5 mol (preferably from 1.2 to 3 mol), of formaldehyde. It is advantageous to employ an excess of bromide or hydrogen bromide, for example from 1.2 to 10 mol (preferably from 2 to 5 mol), of a bromide or hydrogen bromide per mole of trifluoromethoxybenzene. Suitable for use as solvents are, for example, alcohols or carboxylic acids. Preference is given to methanol and acetic acid. The reaction temperature for this step can be varied within a relatively wide range. It can, for example, be between 0 and 100° C., preferably between 20 and 90° C. Work-up of the reaction mixture that is present after the reaction can be carried out, for example, by pouring the mixture into ice water, extraction with an organic solvent (for example, a water-immiscible ether, preferably methyl tert-butyl ether), concentration of the organic extract and distillation of the residue.

In a completely analogous manner, it is possible to prepare 4-chloromethyl-1-trifluoromethoxybenzene from trifluoromethoxybenzene by using hydrogen chloride or chlorides (for example, sodium chloride) instead of hydrogen bromide or bromides.

The second step of the process according to the invention, the halogen-cyano exchange, can be carried out, for example, using sodium cyanide or potassium cyanide in aqueous alcohol. Preferably, 4-bromomethyl- or 4-chloromethyl-1-trifluoromethoxybenzene is reacted with sodium cyanide in an alcohol/water mixture to give (4-trifluoromethoxyphenyl)acetonitrile. The alcohol/water mixture may, for example, comprise alcohol and water in a volume ratio of from 2 to 10:1, preferably from 3 to 8:1. Suitable alcohols are, for example, $C_1$–$C_4$-alkyl alcohols, such as methanol and ethanol. The cyanide can be employed, for example, in an amount of from 1 to 10 mol, based on 1 mol of 4-bromomethyl- or 4-chloromethyl-1-trifluoromethoxybenzene. This amount is preferably from 1 to 2 mol. The reaction temperature for this step can be varied within a relatively wide range. It can, for example, be between 0 and 100° C., preferably between 20 and 90° C. Work-up of the reaction mixture that is present after the halogen-cyano exchange can be carried out, for example, by pouring the mixture into water, extracting with a water-immiscible organic solvent, concentrating the organic extract and distilling the residue.

For the third step of the process according to the invention, the reduction of the (4-trifluoromethoxyphenyl)acetonitrile to 2-(4-trifluoromethoxyphenyl)ethylamine using hydrogen in the presence of a nickel catalyst, the preferred catalyst being Raney nickel. Suitable for use as solvents are ethers, such as dioxane or tetrahydrofuran, or alcohols, such as methanol or isopropanol. To suppress the formation of secondary amines, it may be advantageous to carry out the reaction in the presence of ammonia. Per mole of (4-trifluoromethoxyphenyl)acetonitrile, it is possible to add, for example, from 0.05 to 0.5 mol (preferably from 0.1 to 0.3 mol) of nickel catalyst (calculated as metal). The hydrogen pressure can, for example, be in the range from 50 to 200 bar and is preferably between 90 and 140 bar. The reaction temperature for this step can be varied in a wide range, for example, between 50 and 200° C., preferably between 80 and 130° C. Work-up of the reaction mixture that is present after the hydrogenation can be carried out, for example, by initially filtering off the catalyst and then subjecting the filtrate to a distillation.

Using the process according to the invention, it is possible to prepare 2-(4-trifluoromethoxyphenyl)ethylamine from the readily accessible trifluoromethoxybenzene in a process that is easy to realize on an industrial scale, and in good yields. Over all reaction steps, the yield is considerably higher than 40% of theory. Handling of molecular moieties that have to be cleaved off again and the use of expensive Pd catalysts are avoided.

The present invention furthermore relates to an advantageous process for preparing 4-bromomethyl- and 4-chloromethyl-1-trifluoromethoxybenzene where trifluoromethoxybenzene is converted by bromo-or chloromethylation into 4-bromomethyl- or 4-chloromethyl-1-trifluoromethoxybenzene. The practice of this reaction is described above as the first step in the process for preparing 2-(4-trifluoromethoxyphenyl)ethylamine. In the manner found here, 4-bromomethyl- and 4-chloromethyl-1-trifluoromethoxybenzene are obtainable in a one-step process in yields of 60% and more, which is a considerable improvement compared to the prior art processes for preparing these chemicals.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1

4-Bromomethyl-1-trifluoromethoxybenzene 300 g of trifluoromethoxybenzene, 111 g of paraformaldehyde, 456 g of sodium bromide, and 900 ml of glacial acetic acid were initially charged and heated at 90° C. To release hydrogen bromide, a mixture of 450 ml of glacial acetic acid and 678 g of concentrated sulfuric acid was then added dropwise. After the addition had ended, the reaction mixture was stirred at 90° C. for 20 hours. The reaction mixture was then poured onto 1,000 g of ice and extracted twice with in each case 300 ml of methyl tert-butyl ether. The combined organic extracts were washed with 100 ml of water and concentrated. The residue was distilled at 20 hPa in a spinning band column. This gave 324.3 g of 4-bromomethyl-1-trifluoromethoxybenzene as a colorless liquid (60% of theory) of b.p. 82–83° C.

Example 2

4-Chloromethyl-1-trifluoromethoxybenzene 200 g of trifluoromethoxybenzene and 48 g of paraformaldehyde were dissolved in 500 ml of methanol, and dry hydrogen chloride gas was introduced at 60° C. for 7 hours. The waste gases were, via a reflux condenser, passed into aqueous ammonia. The reaction mixture was then poured onto 1,000 g of ice and extracted twice with in each case 300 ml of methyl tert-butyl ether. The combined extracts were washed with 100 ml of water and then with 100 ml of sodium bicarbonate solution and subsequently concentrated. The residue was distilled at 18 hPa in a spinning band column. This gave 158.8 g of 4-chloromethyl-1-trifluoromethoxybenzene as a colorless liquid (65% of theory) of b.p. 71–74° C.

Example 3

(4-Trifluoromethoxyphenyl)acetonitrile 150 g of ethanol, 28 ml of water, and 31.5 g of sodium cyanide were initially charged, and 127.5 g of 4-bromomethyl-1-trifluoromethoxybenzene were added. The reaction mixture was stirred at 90° C. for 3.5 hours and then poured into 250 ml of water and extracted twice with 50 ml portions of dichloromethane. The combined organic phases were concentrated and the residue was distilled at 18 hPa. This gave 81.5 g of (4-trifluoromethoxyphenyl)acetonitrile as a colorless liquid (76.3% of theory) of b.p. 110–112° C.

Example 4

(4-Trifluoromethoxyphenyl)acetonitrile

The procedure of Example 3 was repeated, but using the equivalent amount of 4-chloromethyl-1-trifluoromethoxybenzene. Following distillation, (4-trifluoromethoxyphenyl)acetonitrile was obtained as a colorless liquid in a yield of 65% of theory, b.p. 109–111° C.

Example 5

2-(4-Trifluoromethoxyphenyl)ethylamine 650 ml of methanol, 260 g of (4-trifluoromethoxyphenyl)acetonitrile, and moist Raney nickel in an amount corresponding to 0.39 mol were initially charged in an autoclave, and 260 ml of ammonia were condensed in. The mixture was hydrogenated at 130° C. and a hydrogen pressure of 140 bar for 2 hours. The reaction mixture was then vented at room temperature, and the catalyst was filtered off. The filtrate was distilled at 10 hPa. This gave 224.5 g of 2-(4-trifluoromethoxyphenyl)ethylamine as a colorless liquid (86.7% of theory) of b.p. 84–86° C.

What is claimed is:

1. A process for preparing 2-(4-trifluoromethoxyphenyl)ethylamine comprising (a) converting trifluoromethoxybenzene by halomethylation into 4-halogenomethyl-1-trifluoromethoxybenzene, (b) converting the 4-halogenomethyl-1-trifluoromethoxybenzene by halogen-cyano exchange into (4-trifluoromethoxy)acetonitrile, and (c) reducing the (4-trifluoromethoxy)acetonitrile using hydrogen in the presence of a nickel catalyst to form 2-(4-trifluoromethoxyphenyl)ethylamine.

2. A process according to claim 1 wherein the halomethylation is carried out using formaldehyde and (a) hydrogen bromide, optionally in the presence of a Lewis acid and/or a protic acid as catalyst, or (b) hydrogen bromide released from a bromide using a strong acid, or (c) sodium bromide in the presence of a Lewis acid and/or a protic acid as catalyst.

3. A process according to claim 1 wherein the halomethylation is carried out using from 1 to 5 mol of formaldehyde and from 1.2 to 10 mol of hydrogen bromide or a bromide per mole of trifluoromethoxybenzene at from 0 to 100° C.

4. A process according to claim 1 the halomethylation is carried out using from 1 to 5 mol of formaldehyde and from 1.2 to 10 mol of hydrogen chloride or a chloride per mole of trifluoromethoxybenzene at from 0 to 100° C.

5. A process according to claim 1 wherein the halogen-cyano exchange is carried out using sodium cyanide or potassium cyanide in aqueous alcohol at temperatures in the range from 0 to 100° C.

6. A process according to claim 1 wherein the nickel catalyst is Raney nickel in an amount of from 0.05 to 0.5 mol (calculated as metal) per mole of (4-trifluoromethoxyphenyl)acetonitrile.

7. A process according to claim 1 wherein the reduction is carried out at hydrogen pressures in the range from 50 to 200 bar and at temperatures in the range from 50 to 200° C.

* * * * *